(12) United States Patent
Mohamed

(10) Patent No.: US 8,052,685 B2
(45) Date of Patent: Nov. 8, 2011

(54) INTRAMEDULLARY DEVICE AND METHOD OF USE

(76) Inventor: Hossam Abdel Salam El Sayed Mohamed, Philadelphia, PA (US)

( * ) Notice: Subject to any disclaimer, the term of this patent is extended or adjusted under 35 U.S.C. 154(b) by 134 days.

(21) Appl. No.: 12/708,952

(22) Filed: Feb. 19, 2010

(65) Prior Publication Data

US 2011/0208188 A1 Aug. 25, 2011

(51) Int. Cl.
*A61B 17/70* (2006.01)
(52) U.S. Cl. .............. 606/62; 606/64; 606/280
(58) Field of Classification Search .............. 606/62–68, 606/280, 287, 71, 281, 286, 86 R, 170, 180, 606/80, 96, 79; 623/20.11; 408/227
See application file for complete search history.

(56) References Cited

U.S. PATENT DOCUMENTS

| | | | |
|---|---|---|---|
| 4,237,875 A | 12/1980 | Termanini | |
| 5,810,820 A | 9/1998 | Santori et al. | |
| 6,168,599 B1 * | 1/2001 | Frieze et al. | 606/80 |
| 6,488,684 B2 * | 12/2002 | Bramlet et al. | 606/62 |
| 6,575,973 B1 | 6/2003 | Shekalim | |
| 7,828,802 B2 * | 11/2010 | Levy et al. | 606/63 |
| 7,879,036 B2 * | 2/2011 | Biedermann et al. | 606/62 |
| 2002/0161369 A1 | 10/2002 | Bramlet et al. | |
| 2006/0229617 A1 | 10/2006 | Meller et al. | |

FOREIGN PATENT DOCUMENTS

| | | |
|---|---|---|
| EP | 0922437 A1 | 6/1999 |
| WO | 2009150691 A1 | 12/2009 |

OTHER PUBLICATIONS

International Search Report for PCT/IB2011/000150 mailed Jun. 21, 2011.

* cited by examiner

*Primary Examiner* — Pedro Philogene
(74) *Attorney, Agent, or Firm* — Caesar, Rivise, Bernstein, Cohen & Pokotilow, Ltd.

(57) ABSTRACT

An intramedullary rod and system for introducing it into a longitudinally extending bore in the bone of a patient is disclosed. The system includes a guide tube, a cutter assembly and the intramedullary rod. The guide tube has a central passageway and a plurality of longitudinally extending slots and is arranged to be located within the bore in the bone. The cutter assembly includes a body member having a plurality of blades extending outward therefrom and is arranged to be moved along the central passageway of the guide tube so that the blades extend outward through the slots to produce a respective grooves in the bore of the bone of the patient. The intramedullary rod is an elongated linear member having a plurality of longitudinally extending ribs projecting outward therefrom and is arranged to be disposed within the central passageway in the guide tube whereupon its ribs extend through respective ones of the slots in the guide tube for disposition within respective ones of the longitudinal grooves in the bore of the bone of the patient to thereby fix the intramedullary rod therein.

14 Claims, 4 Drawing Sheets

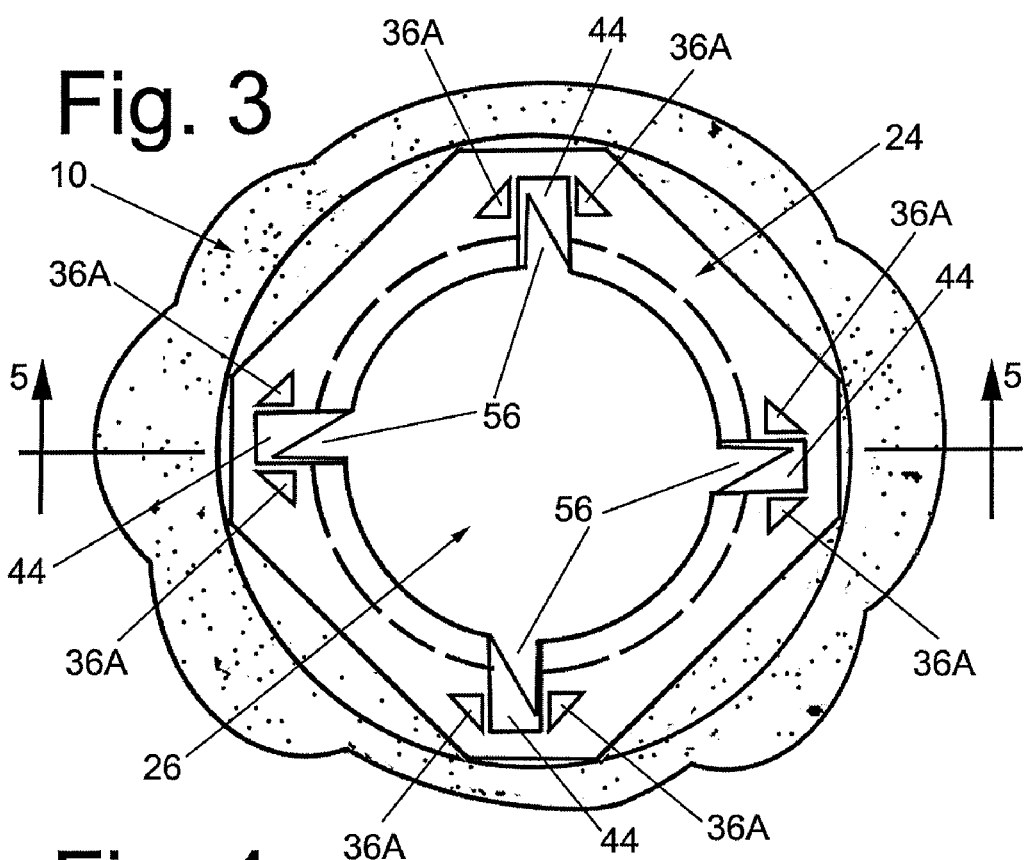
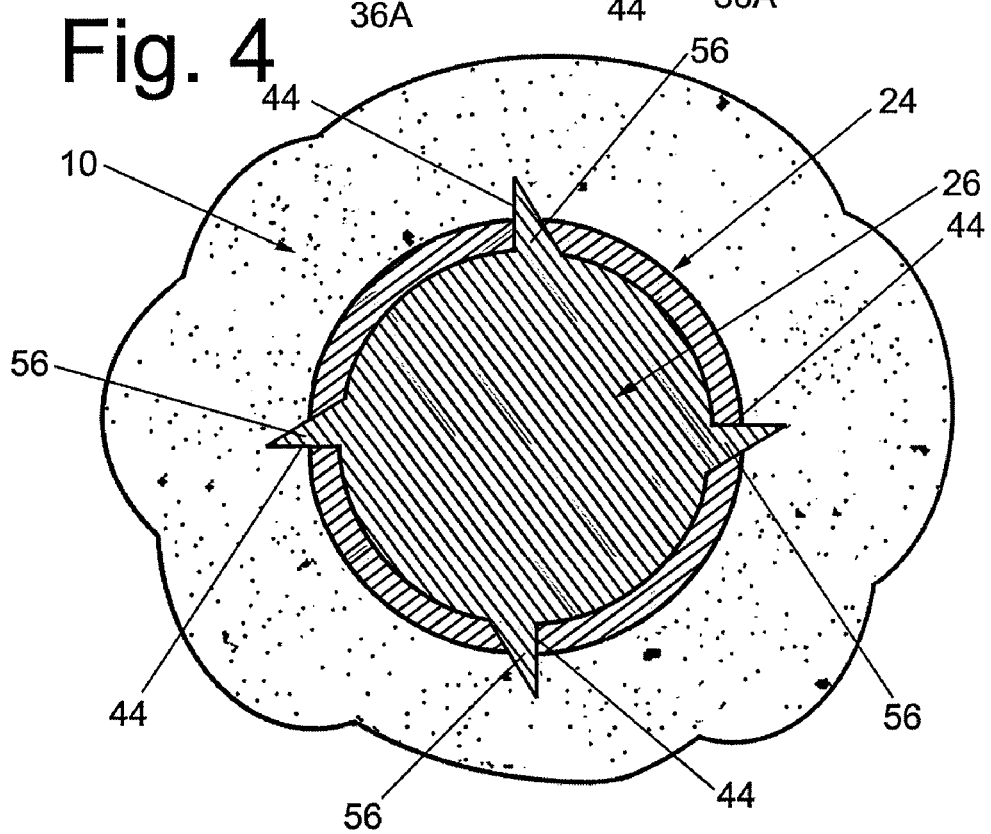

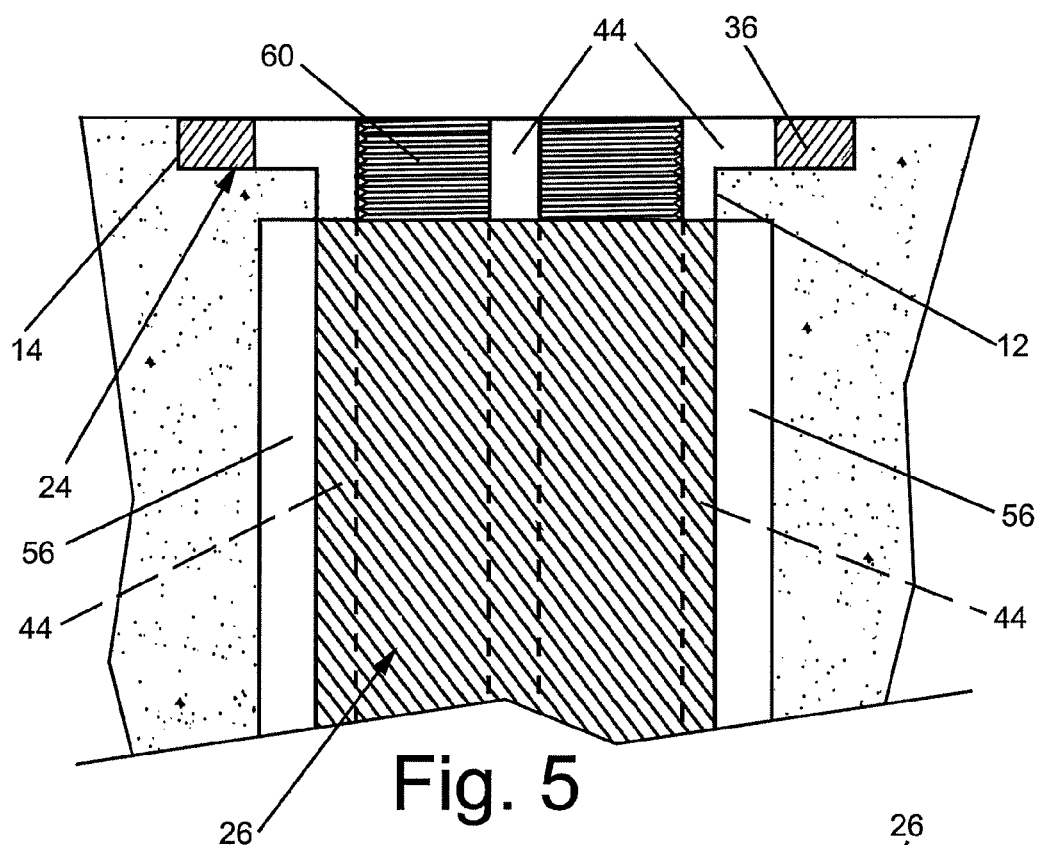
Fig. 5
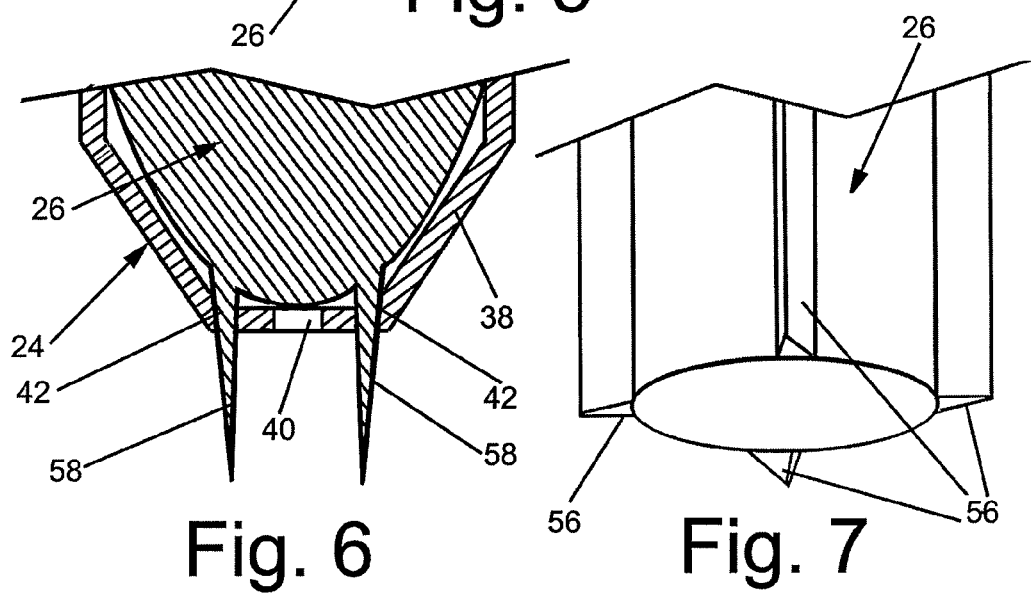
Fig. 6
Fig. 7

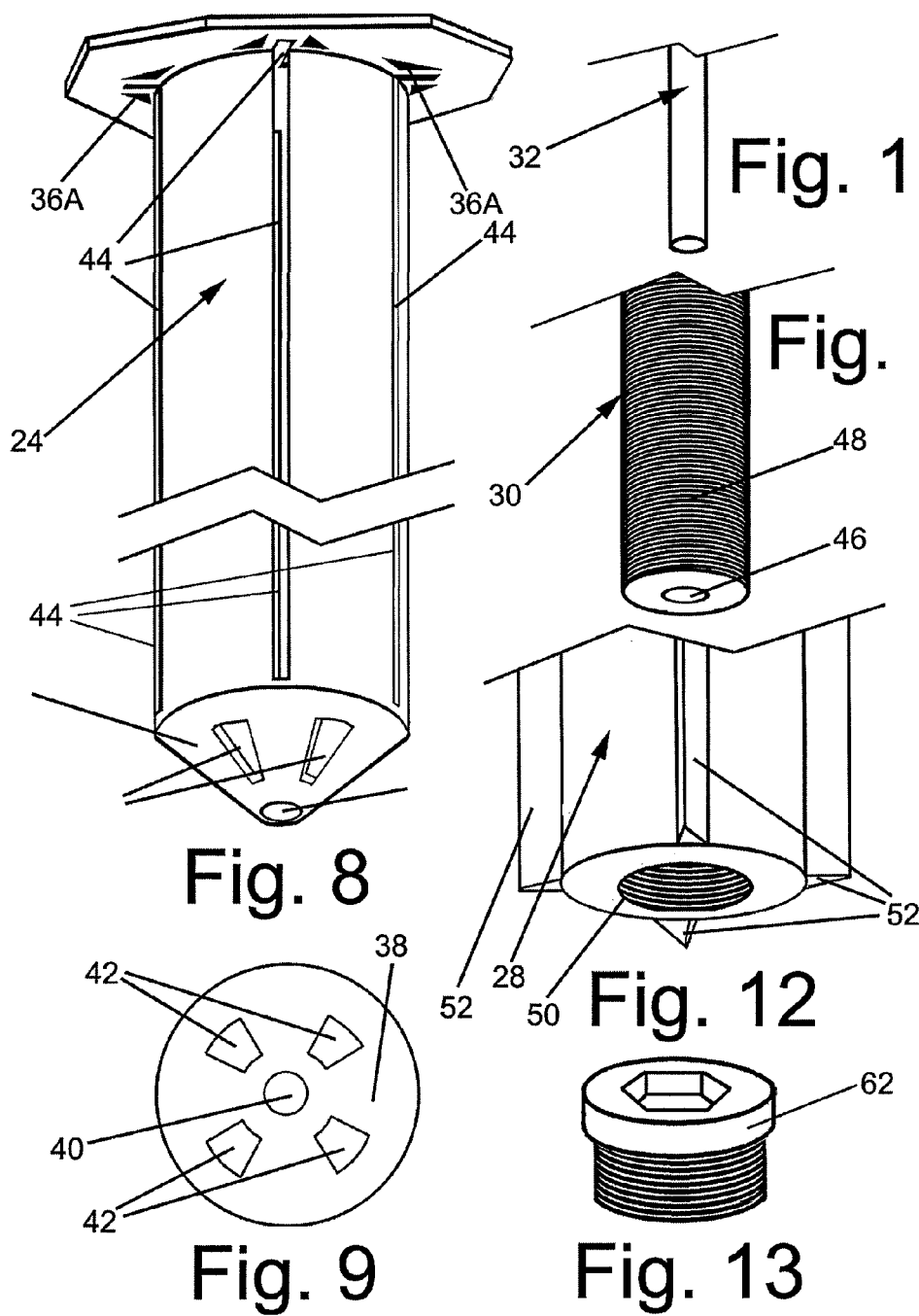

INTRAMEDULLARY DEVICE AND METHOD OF USE

CROSS-REFERENCE TO RELATED APPLICATIONS

"Not Applicable"

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

This invention relates generally to medical devices and more particularly to systems for introducing an intramedullary rod into a bone of a patient.

BACKGROUND OF THE INVENTION

As is known, intramedullary rods (also referred to as intramedullary nails) are used in orthopedics to align and stabilize fractures. Such rods are typically inserted into the bone marrow canal or bore in the center of the long bones of the extremities (e.g., the femur or tibia). One of the significant advantages of such rods over other methods of fixation is that they share the load with the bone, rather that entirely support the bone. Because of this, patients are able to use the extremity more quickly. Typically such rods are fixed in position via the use of transversely extending locking screws. While generally effective for its purpose, transversely extending screw-based fixation techniques have drawbacks, namely, placement and fixation is relatively difficult and time consuming and as a result the patient will be exposed to larger doses of radiation resulting from the imaging procedure during the rod's placement and fixation. Moreover, the use of transversely extending locking screws places unnecessary stress at the screw contact points.

Accordingly, a need exists for an intramedullary device that overcomes the disadvantages of the prior art.

The subject invention addresses that need by providing an intramedullary device which obviates the need for transversely extending locking screws and their attendant problems. Thus, the device of this invention enables its placement and fixation to be accomplished in a shorter period of time than with prior art devices. Moreover, due to its biomechanical properties the device of this invention exhibits a more even distribution of stress along its length, thereby facilitating faster healing. Further still, dynamization (i.e., the promotion of bone healing in fractures by allowing some movement or compressive loading) begins to occur from the first day of fixation to thereby further enhance the rate of healing and callus formation and without scarring of the skin as has characterized the to prior art.

SUMMARY OF THE INVENTION

In accordance with one aspect of the invention there is provided an intramedullary rod and system for introducing it into a longitudinally extending bore in the bone of a patient. The system basically comprises a guide tube, a cutter assembly and an intramedullary rod. The guide tube is preferably in the form of an elongated tubular member having a central passageway and a plurality of longitudinally extending slots communicating with the central passageway and is arranged to be located within the bore in the bone of the patient to extend therealong. The cutter assembly is preferably in the form of a body member having a plurality of blades extending outward therefrom. The body member is arranged to be disposed within the central passageway of the guide tube with the plurality of blades extending outward through respective slots in the guide tube. The body member is arranged to be moved longitudinally along the guide tube, e.g., driven therealong by a drive screw extending over a longitudinally extending guide-wire, whereupon the blades produce a plurality of longitudinal grooves in the bore of the bone of the patient. The intramedullary rod is preferably in the form of an elongated linear member having a plurality of longitudinally extending ribs projecting outward therefrom.

The intramedullary rod is arranged to be disposed within the central passageway in said guide tube, whereupon its ribs extend through respective ones of the slots in the guide tube for disposition within respective ones of the longitudinal grooves in the bore of the bone of the patient to thereby fix the intramedullary rod therein.

In accordance with another aspect of this invention there is provided a method for deploying the medullary rod into the bone of a patient. To that end the method basically comprises disposing a guide tube like described above into the bore in the bone of the patient so that it extends therealong. A body member of a cutter assembly, like that described above, is then introduced within the central passageway of the guide tube so that the plurality of blades extend outward through respective slots in the guide tube and is moved longitudinally along the guide tube, so that the blades produce a plurality of longitudinal grooves in the bore of the bone of the patient. The body member is then removed from the guide tube and an intramedullary rod, like that described above, is introduced within the central passageway in the guide tube, whereupon its ribs extend through respective ones of the slots in the guide tube for disposition within respective ones of the longitudinal grooves in the bore of the bone of the patient to thereby fix the intramedullary rod therein.

DESCRIPTION OF THE DRAWING

FIG. 3 is a top plan view of the proximal end of the bone of the patient, showing the guide tube and an intramedullary rod forming another portion of this invention in place within the bone of the patient;

FIG. 4 is a transverse sectional view of the guide tube with the intramedullary rod in place taken along a section line between the proximal end of the guide tube and the distal end of the guide tube;

FIG. 5 is an enlarged longitudinal sectional view taken along line 5-5 of FIG. 3;

FIG. 6 is a longitudinal sectional view of the distal end of the guide tube and intramedullary rod showing its barbs (spikes) for penetration into the cancellous (spongy) portion of the bone to anchor the rod in place;

FIG. 7 is an isometric view of a portion of the intramedullary rod shown in FIGS. 3 and 4;

FIG. 8 is an isometric view, partially broken away, of the guide tube shown in FIGS. 1-5.

FIG. 9 is an end view of the distal end of the guide tube shown in FIGS. 1-5 and 7;

FIG. 10 is an isometric view of a portion of the guide wire shown in FIG. 1;

FIG. 11 is an isometric view of a portion of the drive screw shown in FIG. 1;

FIG. 12 is an isometric view of a portion of the cutter shown in FIG. 1; and FIG. 13 is an isometric view of a cap for sealing the interior of the guide tube.

DETAILED DESCRIPTION OF THE PREFERRED EMBODIMENT

Figure 1:
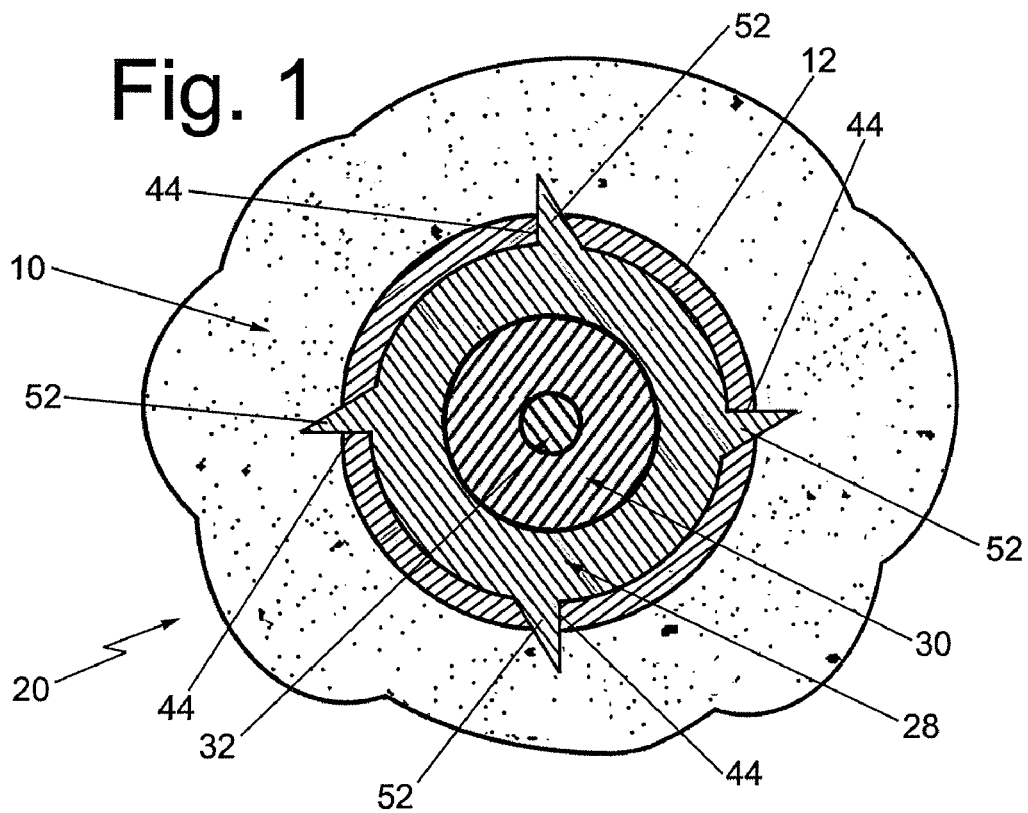
FIG. 1 is a transverse sectional view showing some of the components of the device of this invention, namely a guide tube, a cutter, a drive screw and a guide wire, shown in position within a bore in the bone of a patient.

Referring now to the various figures of the drawing wherein like reference characters refer to like parts, there is shown in FIG. 1 at 20 a system including a device in the form of a guide tube 24 and an associated intramedullary rod 26 (FIGS. 3-7) for introduction into a bore in a bone 10, e.g., femur, of a patient. The system 20 additionally comprises a cutter assembly in the form of a cutter 28 (FIGS. 1 and 12), a drive screw 30 (FIGS. 1 and 11) and a guide wire 32 (FIG. 10). The cutter assembly serves to prepare the bone for the introduction of the guide tube and intramedullary rod therein. In particular, the cutter assembly is arranged to create a plurality of longitudinally extending grooves in the bore within the bone. Those grooves are arranged to receive respective ones of longitudinally extending ribs (to be described later) of the intramedullary rod so that when the rod is located within the bore the ribs prevent rotation of the intramedullary rod in the patient's bone. This fixes the intramedullary rod in place without the need for conventional screws or other fasteners extending radially through the bone.

The guide tube 24 is best seen in FIG. 8 and basically comprises an elongated hollow tubular member having circular sidewall 34. The proximal end of the guide tube is in the form of a square flange 36 whose corners are cut away diagonally (see FIG. 3). The distal end 38 of the guide tube is conical and includes a central opening 40 sized to accommodate the guide wire 32 and a plurality of apertures or openings 42 disposed about the central opening 40. The guide tube includes a plurality, e.g., four, longitudinally extending slots 44 in its sidewall. The slots 44 start at the top surface of the flange 36 and terminate just before the conical distal end 38 of the guide tube. As best seen in FIG. 3 a plurality of triangular shaped apertures or holes 36A are provided in pairs in the flange spaced on opposite sides of the entry to each of the slots 44.

The guide tube 24 is arranged to be introduced into a longitudinal bore 12 (FIG. 5) created in the patient's bone 10. To that end, the interior of the bone is reamed in a conventional manner to create the bore 12. In addition to creating the bore a recess 14 (FIG. 5) is created in the proximal end of the bone 10 at the bore 12 to accommodate the flange 36 of the guide tube 24. The guide tube is then forced into the bore 12 by an applicator (not shown) so that the outside surface of the guide tube's sidewall engages the inner surface of the bore in the bone and the flange 36 is within the recess 14. The applicator is a conventional device which is modified to include a socket for receipt of the flange 36 of the guide tube. In addition, the applicator includes a plurality of projections which extend into its socket and which are adapted to be received within correspondingly shaped apertures 36A in the guide tube's flange.

The details of the cutter assembly will now be described. To that end, as best seen in FIG. 10, the guide wire 32 is of a conventional construction, e.g., is a flexible elongated member. The drive screw 30 is best seen in FIG. 11 and basically comprises a rod-like member having a central longitudinally extending passageway 46 for receipt of the guide wire 32 so that the guide wire can be extended through it. The outer surface of the drive screw includes a helical thread 48. The drive screw 30 is arranged to be coupled to a motor (not shown) for rotating it at high rate of speed. The cutter 28 is best seen in FIGS. 1 and 12 and basically comprises an elongated rod-like member whose outside diameter is just slightly less than the inside diameter of the sidewall of the guide tube 24. The cutter 28 includes a central passageway 50 which is internally threaded to cooperate with the external threads on the drive screw. A plurality, e.g., four, equidistantly spaced, longitudinally extending blades 52 project outward from the cutter. The blades are shaped and sized to fit within respective ones of the slots 44 in the guide tube.

Once the guide tube 24 is in place, the cutter assembly is introduced therein. In particular, the guide wire 32 is extended through the interior of guide tube 24 to pass through its central opening 40. The cutter 28 with the drive screw 30 extending therethrough is threaded on the guide wire 32 so that the respective blades 52 of the cutter extend into respective slots 44 in the guide tube. The drive screw 30 is than rotated by the motor (not shown) to which it is coupled to move the cutter along the guide wire the distal direction down the interior of the guide tube. The slots 44 guide this movement.

Figure 2:
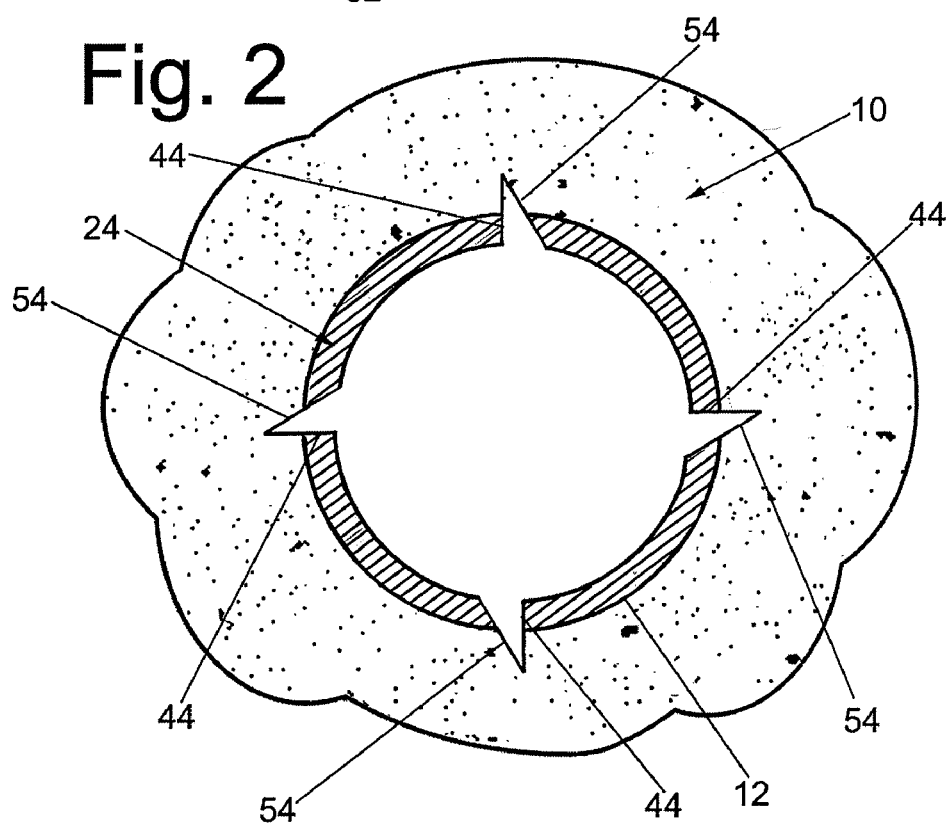
FIG. 2 is a transverse sectional view similar to FIG. 2, but showing the guide tube after the cutter, drive screw and guide wire have been removed.

As can best be seen in FIG. 1 the blades 52 extend beyond the outer periphery of the guide tube. Thus, the movement of the cutter down the guide tube causes the blades 52 to create respective longitudinally extending grooves 54 (FIG. 2) in the periphery of the bore 12 in the patient's bone. Once the grooves 54 are created the cutter assembly is removed from the guide tube, leaving the guide tube in place, like shown in FIG. 2.

The guide tube 24 is now ready to receive the intramedullary nail or rod 26. The rod 26 is best shown in FIGS. 3-7 and basically comprises an elongated cylindrically shaped, solid member whose outside diameter is just slightly less than the inside diameter of the sidewall of the guide tube. A plurality, e.g., four, equidistantly spaced, longitudinally extending ribs 56 project outward from the intramedullary rod. The ribs 56 are shaped and sized to fit within respective ones of the grooves 54 that were created by the cutter. The distal end of the intramedullary rod is best seen in FIG. 6 and is of a dome-like configuration. It includes a plurality, e.g., four, longitudinally extending barbs or spikes 58 projecting distally parallel to the longitudinal axis of the rod. The spikes are arranged to penetrate into the cancellous portion of the bone at the distal end of the bore to seat the rod in place and prevent its longitudinal movement (while permitting some dynamization to be accomplished). To that end, the spikes are oriented so that each passes through a respective aperture 42 in the conical distal end of the guide tube.

The intramedullary rod 26 is deployed by introducing its distal end into the proximal end of the seated guide tube and with the ribs 56 of the rod aligned with the slots 44 of the guide tube. A force is then applied to the rod to drive it down the interior of the guide tube until its barbs 58 extend out of the apertures 42 in the distal end of the guide tube and into the cancellous portion of the bone. The rod 26 is sized so that when in that position its proximal end will be recessed within the guide tube as shown in FIG. 5. As can be seen therein the proximal end of the hollow interior passageway of the guide tube includes internal threads 60. These threads are arranged to receive cooperating external threads on a cap 62 (FIG. 13) which is used to seal the rod 26 within the guide tube.

It should be pointed out that the shape, size and number of the blades of the cutter as shown herein is merely exemplary and thus other blade arrangements are contemplated. Moreover the shape of the slots in the guide tube is exemplary. Thus other shaped slots can be provided so long as the blades can pass therethrough. Further still other means can be used to drive the cutter down the guide tube in lieu of the drive screw, if desired.

As should be appreciated by those skilled in the art the placement of the ribbed intramedullary rod within the patient bone can be accomplished relatively quickly and easily. Moreover the ribs of the intramedullary rod create a myriad of continuous contact points along the length of the grooves in the bone in which the ribs are seated. This action serves to prevent relative rotation of the rod within the bone while distributing stress over a much greater area than the prior art. Moreover, while the ribs prevent rotation of the rod within the bore, they do not prevent microscopic longitudinal movement, nor do the spikes within the cancellous portion of the bone. Accordingly, with the subject invention the intramedullary rod can be moved microscopically longitudinally to effect immediate dynamization and more rapid healing, a feature which is not possible with prior art techniques. Further still, the subject invention enables the use of imaging radiation to be limited to only in the very beginning of detection of the medulla and insertion of the guide wire in the distal segment, thereby offering the patient less exposure to radiation.

Without further elaboration the foregoing will so fully illustrate my invention that others may, by applying current or future knowledge, adopt the same for use under various conditions of service.

I claim:

1. An intramedullary rod and system for introducing it into a longitudinally extending bore in the bone of a patient, said system comprising a guide tube, a cutter assembly and an intramedullary rod, said guide tube comprising an elongated tubular member having a central passageway and a plurality of longitudinally extending slots communicating with the central passageway, said guide tube being arranged to be located within the bore in the bone of the patient to extend therealong, said cutter assembly comprising a body member having a plurality of blades extending outward therefrom, said body member being arranged to be disposed within said central passageway of said guide tube with said plurality of blades extending outward through respective slots in said guide tube, said body member being arranged to be moved longitudinally along said guide tube, whereupon said blades produce a plurality of longitudinal grooves in the bore of the bone of the patient, said intramedullary rod comprising an elongated linear member having a plurality of longitudinally extending ribs projecting outward therefrom, said intramedullary rod being arranged to be disposed within said central passageway in said guide tube whereupon said ribs of said intramedullary rod extend through respective ones of said slots in said guide tube for disposition within respective ones of the longitudinal grooves in the bore of the bone of the patient to thereby fix the intramedullary rod therein.

2. The device of claim 1 wherein said cutter assembly additionally comprises a drive screw to move said body member longitudinally along said guide tube.

3. The device of claim 2 wherein said drive screw includes a central opening, said central opening being arranged to receive a guide-wire to guide said cutter assembly through said guide tube.

4. The device of claim 1 wherein said guide tube includes a distal end portion having at least one aperture therein and wherein said intramedullary rod includes a distal end having at least one spike projecting therefrom for extension through said at least one aperture to anchor said distal end of said intramedullary rod into the spongy portion of the bone of the patient contiguous with the bore in the bone of the patient.

5. The device of claim 4 wherein said guide tube also includes a proximal end having a peripheral flange extending from said central passageway, said flange being arranged to be received within a recess formed in the bone of the patient contiguous with the bore therein.

6. The device of claim 5 wherein said flange includes plural holes therein for engagement by associated members of an applicator device.

7. The device of claim 1 wherein said guide tube includes a proximal end having a peripheral flange extending from said central passageway, said flange being arranged to be received within a recess formed in the bone of the patient contiguous with the bore therein.

8. The device of claim 7 wherein said flange also includes plural holes therein for engagement by associated members of an applicator device.

9. The device of claim 5 additionally comprising a threaded cap arranged to be disposed within said central passageway adjacent the proximal end thereof to close said passageway after said intramedullary rod has been disposed within said passageway in said guide tube.

10. The device of claim 7 additionally comprising a threaded cap arranged to be disposed within said central passageway adjacent the proximal end thereof to close said passageway after said intramedullary rod has been disposed within said passageway in said guide tube.

11. A method for introducing a medullary rod into a longitudinally extending bore in the bone of a patient comprising:
    providing a guide tube comprising an elongated tubular member having a central passageway and a plurality of longitudinally extending slots communicating with the central passageway;
    disposing said guide tube into the bore in the bone of the patient so that it extends therealong;
    providing a cutter assembly comprising a body member having a plurality of blades extending outward therefrom;
    introducing said body member within said central passageway of said guide tube so that said plurality of blades extend outward through respective slots in said guide tube and moving said body member longitudinally along said guide tube, whereupon said blades produce a plurality of longitudinal grooves in the bore of the bone of the patient;
    removing said body member from said guide tube;
    providing an intramedullary rod comprising an elongated linear member having a plurality of longitudinally extending ribs projecting outward therefrom; and
    introducing said intramedullary rod within said central passageway in said guide tube, whereupon said ribs of said intramedullary rod extend through respective ones of said slots in said guide tube for disposition within respective ones of the longitudinal grooves in the bore of the bone of the patient to thereby fix the intramedullary rod therein.

12. The method of claim 11 additionally comprising providing a drive screw within said body member to move said body member longitudinally along said guide member.

13. The method of claim 12 additionally comprising providing a guide-wire to guide said body member along said passageway.

14. The method of claim 11 comprising sealing said central passageway in said guide member with a cap after said intramedullary rod has be placed in position.

* * * * *